(12) United States Patent
Woodward et al.

(10) Patent No.: US 10,831,872 B2
(45) Date of Patent: Nov. 10, 2020

(54) AUTOMATED VOICE-ACTIVATED MEDICAL ASSISTANCE

(71) Applicant: Covidien LP, Mansfield, MA (US)

(72) Inventors: Jonathan James Woodward, Annapolis, MD (US); Matthew Sgambato, Baltimore, MD (US); Paul Von der lippe, Boulder, CO (US)

(73) Assignee: Covidien LP, Mansfield, MA (US)

( * ) Notice: Subject to any disclaimer, the term of this patent is extended or adjusted under 35 U.S.C. 154(b) by 256 days.

(21) Appl. No.: 15/973,727

(22) Filed: May 8, 2018

(65) Prior Publication Data

US 2019/0347387 A1 Nov. 14, 2019

(51) Int. Cl.
*G06F 21/32* (2013.01)
*G16H 10/60* (2018.01)
*G10L 17/22* (2013.01)

(52) U.S. Cl.
CPC .............. *G06F 21/32* (2013.01); *G10L 17/22* (2013.01); *G16H 10/60* (2018.01)

(58) Field of Classification Search
CPC .......... G06F 21/32; G16H 10/60; G10L 17/22
See application file for complete search history.

(56) References Cited

U.S. PATENT DOCUMENTS

| | | | | |
|---|---|---|---|---|
| 8,898,804 B2 * | 11/2014 | Roy | ......................... | H04L 51/32 726/28 |
| 9,330,267 B2 * | 5/2016 | Abe | ......................... | G06F 21/60 |
| 2003/0028811 A1 * | 2/2003 | Walker | ...................... | G07C 9/37 726/5 |
| 2006/0089857 A1 * | 4/2006 | Zimmerman | ....... | G06F 21/6245 705/2 |
| 2006/0212452 A1 * | 9/2006 | Cornacchia, III | .. | G06F 16/3343 |
| 2009/0019552 A1 * | 1/2009 | McLaughlin | ...... | G06Q 30/0203 726/27 |
| 2009/0024416 A1 * | 1/2009 | McLaughlin | .......... | G06Q 50/24 705/3 |
| 2010/0023021 A1 * | 1/2010 | Flaherty | ................. | A61B 90/11 606/130 |
| 2010/0063841 A1 * | 3/2010 | D'Ambrosia | .......... | G06Q 10/10 705/3 |
| 2010/0306858 A1 * | 12/2010 | McLaren | ............... | G16H 40/63 726/28 |
| 2014/0379374 A1 * | 12/2014 | Vinals | .................... | G16H 10/60 705/3 |
| 2016/0283737 A1 * | 9/2016 | Soman | .................. | H04L 9/3213 |
| 2017/0093920 A1 * | 3/2017 | Ducatel | ................. | G06F 21/316 |
| 2018/0110475 A1 * | 4/2018 | Shaya | .................... | G16H 10/40 |

(Continued)

*Primary Examiner* — Hee K Song

(57) ABSTRACT

Methods, systems, and devices for voice-activated medical assistance are described. The method may include receiving an indication of an audio request from a user and determining whether a response to the audio request includes medical information associated with a patient. After determining whether the response includes medical information, the medical assistance server may identify an access class of the medical information and a permission level associated with accessing the access class of the medical information. The method may further include determining whether the user is authorized to access the access class based on the permission level and transmitting an indication of the response to the audio request based on determining whether the user is authorized.

18 Claims, 12 Drawing Sheets

(56) References Cited

U.S. PATENT DOCUMENTS

2018/0121623 A1* 5/2018 Boesen ................ G16H 80/00
2018/0211656 A1* 7/2018 Chong ................. G10L 15/22
2018/0218126 A1* 8/2018 Salazar ................ G16H 50/30

* cited by examiner

AUTOMATED VOICE-ACTIVATED MEDICAL ASSISTANCE

BACKGROUND

The following relates generally to voice-activated medical assistance, and more specifically to automated voice-activated medical assistance.

In a healthcare facility such as a hospital, physiological parameters of the patient (e.g., heart rate, respiratory rate, blood pressure) may be monitored by one or more medical devices. The medical devices may be battery powered and may wirelessly transmit measured patient data over a wireless network within the hospital, thereby allowing the patient to move freely through the hospital while being monitored. Clinicians may remotely monitor the patient by accessing the patient data at a central nurse station or on any web enabled device connected to the network (e.g., smartphone or tablet).

The medical devices may be configured to transmit patient data over a network outside of the hospital, thereby allowing the patient to return home and continue patient care outside the hospital. The medical devices may also be configured to transmit patient data over a network inside of the hospital, thereby allowing the clinician to diagnose and treat the patient. Because patient care instructions (e.g., how many medications to take, what medications to take, when to take the medication, etc.) may not be written down at the time of the appointment or the patient may lose the at-home instructions, the patient may miss a medication dose or take the wrong medication dose, which may lead to physiological events that could put the patient at risk.

SUMMARY

The described features generally relate to methods, systems, devices, or apparatuses that support automated voice-activated medical assistance. A medical assistance server may receive an audio request from a user (e.g., patient, clinician, person associated with the patient), where the audio request may include a request for medical information related to the patient (e.g., a lab result, request for the patient's heart rate, etc.). The medical assistance server may then determine if the response to the audio request includes medical information associated with the patient or if the response includes non-medical information associated with the patient (e.g., an appointment confirmation, initiation of a phone call with a clinician, etc.). Based on this determination, the medical assistance server may identify an access class to access the medical information and a permission level to authorize the user to access the medical information. The access class and permission level may be based on a level of security associated with disclosing the medical information to the patient or a person associated with the patient. Before transmitting the response to the audio request, the medical assistance server may determine whether the user is authorized to access the medical information. If the user is authorized, the medical assistance server may transmit the response to the audio request to the user.

A method for voice-activated medical assistance is described. The method may include receiving an indication of an audio request from a user, determining whether a response to the audio request includes medical information associated with a patient, identifying an access class of the medical information and a permission level associated with accessing the access class of the medical information, determining whether the user is authorized to access the access class based at least in part on the permission level, and transmitting an indication of the response to the audio request based at least in part on determining whether the user is authorized.

Some examples of the method described herein may further include operations, features, means, or instructions for selecting an authentication method based at least in part on the access class of the medical information, the permission level, or both, wherein determining whether the user is authorized to access the access class comprises authenticating the user based at least in part on the selected authentication method. In some examples of the method described herein, the authentication method comprises a voice recognition analysis of the audio request, a facial recognition analysis of the user, determining a proximity of the user to a system that receives the audio request, or a combination thereof.

The method may further include requesting an authorization credential associated with the user, wherein the authorization credential comprises a finger print scan, a pin code input, or both. Some examples of the method described herein may further include operations, features, means, or instructions for identifying a confidence level associated with the determining whether the user is authorized to access the access class, wherein the authorization credential is based at least in part on the identified confidence level. The method may further include determining whether the audio request includes a medical information request associated with the patient. Some examples of the method described herein may further include operations, features, means, or instructions for determining whether the medical information associated with the patient is protected by a privacy policy.

Some examples of the method described herein may further include operations, features, means, or instructions for storing the indication of the audio request if the response to the audio request includes medical information associated with the patient and storing the indication of the response to the audio request. The method may further include retrieving the medical information from a database. The method may further include transmitting the indication of the response to a clinician based at least in part on a facial attribute of the user, a voice attribute of the user, or both. Some examples of the method described herein may further include operations, features, means, or instructions for configuring a format of the indication of the response, wherein the format of the indication comprises an audio format, a visual format, or both.

In some examples of the method described herein, the audio request may comprise a request for medical information associated with the user, a request to schedule an appointment with a clinician, a request for medical information associated with a person other than the user, a request to initiate a call with the clinician, or a combination thereof. In other examples of the method described herein, the response may comprise a medical information response associated with the user, an appointment confirmation, a medical information response associated with a person other than the user, a voice-activated phone call, a video conference call, or a combination thereof.

DETAILED DESCRIPTION

Figure 1:
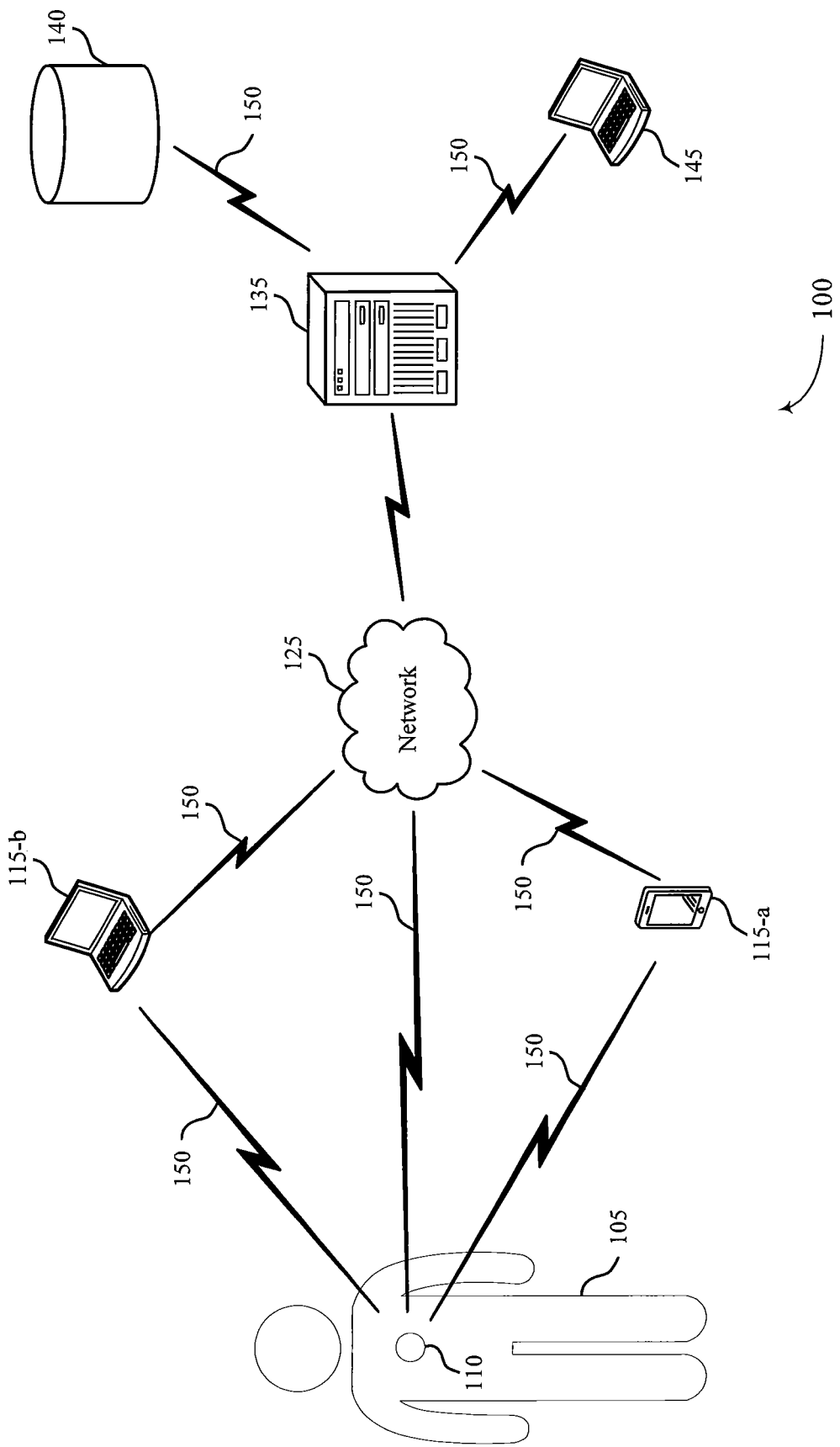
FIG. 1 illustrates an example of a system for medical assistance that supports automated voice-activated medical assistance in accordance with aspects of the present disclosure.

In some home-based patient monitoring systems, a patient may return home from the healthcare facility with instructions on medication type, medication dosage, or time to take the medication. The patient may forget the instructions from the clinician, lose the instructions, or have additional questions for the clinician after returning home. In some cases, the patient or a person associated with the patient may have questions regarding confirmation that the patient attended their appointment with a clinician or took the correct medication. In some hospital-based patient monitoring systems, a patient may receive instructions on medication type, medication dosage, or time to take the medication. The patient may forget the instructions from the clinician or require reminders regarding the instructions.

A system may be implemented in the household or hospital that receives audio input from the patient or a person associated with the patient and automatically answers questions related to the instructions. The audio input may include requests for medical information associated with the patient, requests for non-medical information associated with the patient, requests for appointment confirmations, or a request to contact a clinician, for example. When multiple audio requests are transmitted from multiple users (e.g., the patient or the person associated with the patient), the system may determine the medical relevance of the audio request and the medical information to be included in the response message.

Based on the medical relevance and content of the medical information, a certain level of security may be required to access the information and transmit the response to the person who issued the audio request. The level of security may include a permission level associated with the qualifications of the user to access the information. In some cases, the level of security may also include determining an access class associated with the content of the medical information to be transmitted in the response. Additional levels of security may also include requiring an authorization credential from the user or determining the proximity of the user to the system receiving the audio request.

In some cases, the system may perform voice recognition to validate the user to access the medical information requested. For example, the patient may ask for a heart rate or a blood glucose level at the time of the request. The system may authenticate the user based on the voice recognition and transmit the message including the patient's current heart rate or current blood glucose level based on the authentication to respond with the medical information requested. However, if the system is unable to authenticate the user based on voice recognition, then the system may require an additional level of security for the person to receive the response.

In some examples, the content of the audio request may be tagged according to words, phrases, or voice attributes to determine the level of access to the medical information requested. For example, if the content of the audio request is tagged as related to medical information associated with the patient, the user may require authorization before receiving the response. The system may also store the tagged content for future uses if the patient, clinician, or person associated with the patient requests the same medical information associated with the patient more than once. In other examples, the content tagged as non-medically relevant may be stored in a cloud source that utilizes a cloud-based key (e.g., requires less security to access the information). Alternatively, content tagged as medically relevant may be stored in a security domain and protected with a non-promise key (e.g., require increased security to access the information).

The system may transmit a response to the audio request after the user is authorized to receive the medical information associated with the patient. The response may be an example of an appointment confirmation, a call with a clinician, or medical information associated with the patient. Therefore, the response including medical information associated with the patient may be transmitted to a user that is authorized, and prevents the release of medical information to an unauthorized user.

Aspects of the disclosure are initially described in the context of a wireless patient monitoring system. Aspects of the disclosure are further illustrated by and described with reference to apparatus diagrams, system diagrams, and flowcharts that relate to automated voice-activated medical assistance.

FIG. 1 illustrates an example of a wireless patient monitoring system 100 in accordance with various embodiments of the present disclosure. The wireless patient monitoring system 100 may include a patient 105 wearing, carrying, or otherwise coupled with a medical device 110. Although a single medical device 110 is shown, multiple medical devices 110 may be coupled to the patient 105. The patient 105 may be a patient in a hospital, nursing home, home care, a medical facility, another care facility, or at a home residence. The medical device 110 may transmit signals via wireless communications links 150 to computing devices 115 or to a network 125.

The medical device 110 may include one or more sensors configured to collect a variety of physiological parameters as well as information related to the location and movement of the patient 105. For example, the medical device 110 may include a pulse oximetry (SpO2) sensor, a capnography sensor, a heart rate sensor, a blood pressure sensor, an electrocardiogram (ECG) sensor, a respiratory rate sensor, a glucose level sensor, a depth of consciousness sensor, a body temperature sensor, an accelerometer, a global positioning sensor, a sensor which triangulates position from multiple local computing devices 115, or any other sensor configured to collect physiological, location, or motion data associated with the patient 105. In some examples, medical device 110 may be wired to patient 105. For example, patient 105 may be monitored by a ventilator or a capnography sensor (e.g., medical device 110) that is physically connected to patient 105.

The medical device 110 may be coupled with the patient 105 in a variety of ways depending on the data being collected. For example, the medical device 110 may be directly coupled with the patient 105 (e.g., physically connected to the patient's chest, worn around the patient's wrist, attached to the patient's finger, or positioned over the patients nose or mouth). The data collected by the medical device 110 may be wirelessly transmitted to either the computing devices 115 or to the remote computing device 145 (via the network 125 and central station 135). Data transmission may occur via, for example, frequencies appropriate for a personal area network (such as Bluetooth, Bluetooth Low Energy (BLE), or IR communications) or local (e.g., wireless local area network (WLAN)) or wide area network (WAN) frequencies such as radio frequencies specified by IEEE standards (e.g., IEEE 802.15.4 standard, IEEE 802.11 standard (Wi-Fi), IEEE 802.16 standard (Wi-MAX), etc.).

Computing device 115-a may be a wireless device such as a tablet, cellular phone, personal digital assistant (PDA), a dedicated receiver, or other similar device or a spatially distributed network of devices configured to receive signals from the medical device 110. Computing device 115-b may be a wireless laptop computer, a clinician Workstation on Wheels, or a smart hospital bed configured to receive signals from the medical device 110. Computing device 115-b may also be an audio device (e.g., a smart speaker) configured for voice-activated interaction with patient 105. The computing devices 115 may be in communication with a central station 135 via network 125 (e.g., the Internet).

The medical device 110 may also communicate directly with the central station 135 via the network 125. The central station 135 may be a server or a central nurse station located within the hospital or in a remote location (e.g., a server farm). The central station 135 may also be a server or station located within the home of the patient. The central station 135 may be in further communication with one or more remote computing devices 145, thereby allowing a clinician to remotely monitor the patient 105. The central station 135 may also be in communication with various remote databases 140 where the collected patient data may be stored. In some cases, the remote databases 140 include electronic medical records (EMR) applications for storing and sharing patient data. The remote databases may also include patient look-up information and a library of medically relevant language.

In accordance with aspects of the present disclosure, central station 135 may receive an audio request from a user. A user may be patient 105, a clinician, or a person other than patient 105 and the clinician. In some examples, the user may request medically relevant information associated with patient 105. For example, the user (e.g., patient 105) may request a time of an appointment or request a call with the clinician. Central station 135 may then determine whether the response to the audio request includes medically relevant information associated with the patient. Based on the level of security required to access the medical information, central station 135 may identify an access class for a user to access the medical information. Central station 135 may also identify a permission level to access the medical information based on the identity of the user requesting the information. Central station 135 may then determine if the user is authorized to access the information requested and may formulate and transmit the response to the audio request based on the authorization of the user.

Figure 2:
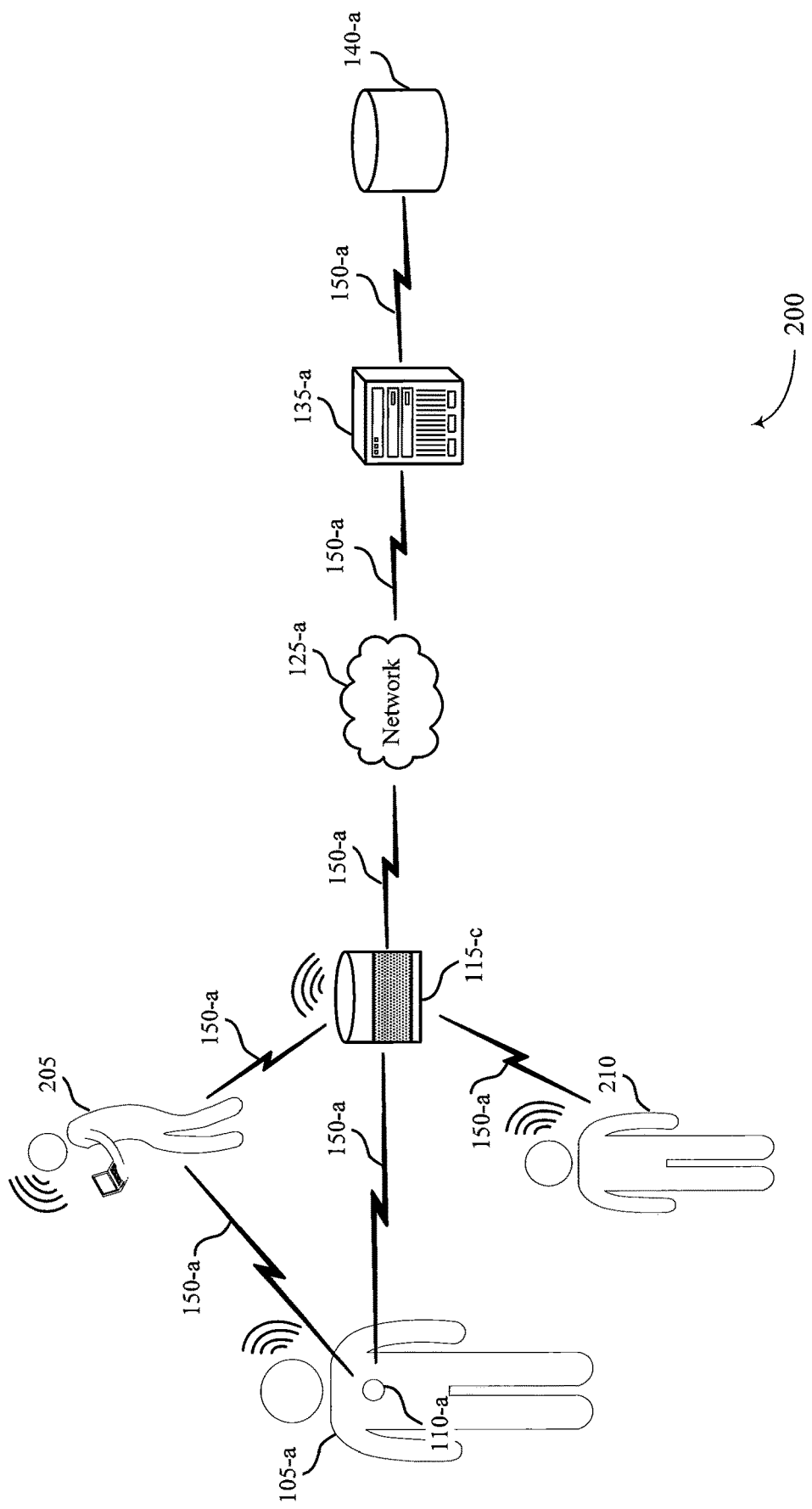
FIG. 2 illustrates an example of a medical assistance system that supports automated voice-activated medical assistance in accordance with aspects of the present disclosure.

FIG. 2 illustrates an example of a medical assistance system 200 that supports automated voice-activated medical assistance in accordance with various aspects of the present disclosure. Medical assistance system 200 may be an example of aspects of wireless patient monitoring system 100 and may include a patient 105-a wearing, carrying, or otherwise coupled with a medical device 110-a. Medical assistance system 200 may also include clinician 205 and user 210 other than clinician 205 and patient 105-a. For example, user 210 may be associated with patient 105-a (e.g., friend, family member, co-worker, etc.).

Patient 105-a may communicate bidirectionally via wired or wireless communication links 150-a to medical audio device 115-c. Medical audio device 115-c may be an example of aspects of computing device 115. Medical audio device 115-c may also be an example of a device that receives an audio request from patient 105-a, clinician 205, or user 210. In some cases, medical audio device 115-c may include a speaker configured to receive the audio request and transmit an audible response (e.g., a smart speaker). In some cases, medical audio device 115-a may include a display screen configured to receive the audio request and transmit a visual response (e.g., initiate a video conference call).

The audio request may include medical information associated with patient 105-a. In some examples, patient 105-a may request medical information associated with medical device 110-a monitoring patient 105-a. For example, patient 105-a may request a report on blood glucose levels or a report of a current heart rate. Patient 105-a may also request lab results from a previous appointment with clinician 205.

The audio request may also include a request for general medical information such as weight, height, age, gender, previous or current medical conditions, currently prescribed medications, or similar medical information that may not be generally associated with a medical device 110-a monitoring the patient 105-a. For example, the audio request may include a request to schedule an appointment with clinician 205 or a request to schedule a call with clinician 205. In some cases, medical assistance server 135-a may automatically trigger a call with clinician 205 based on physical attributes of patient 105-a. For example, medical assistance server 135-a may detect fear, pain, or stress in the voice of patient 105-a, and may activate a phone call or video conference with clinician 205 regardless of the medical information requested.

In some home-based or hospital-based monitoring systems, patient 105-a may forget to take their medications or may not remember the dose of their medications. In that case, patient 105-a may request a reminder to take their medication or the dose of the medication. In some other examples, patient 105-a may ask for a time to take the medication or an amount of the medication to take. Patient 105-a may also send a confirmation indication to medical assistance server 135-a to confirm that the correct dose of medication was taken at the requested time. In some hospital-based monitoring systems, clinician 205 may request the current vitals of patient 105-a or request a time when patient 105-a took the medication.

User 210 may also communicate bidirectionally via wired or wireless communication links 150-a to medical audio device 115-c. In some examples, user 210 may request medical information associated with patient 105-a. For example, user 210 may request lab results from the appointment with clinician 205 or a current medical record associated with patient 105-a. User 210 may also request a report on the health of patient 105-a. For example, user 210 may request a confirmation that patient 105-a attended an appointment with clinician 205 or a confirmation that patient 105-a took their medication.

The audio request may require authorization of the user to access the requested information based on if the response to the audio request includes medical information associated with patient 105-*a*. For example, medical audio device 115-*a* may communicate bidirectionally via wired or wireless communication links 150-*a* to medical assistance server 135-*b* via network 125-*a*. Medical assistance server 135-*a* may also communicate bidirectionally via wired or wireless communication links 150-*a* to database 140-*a* to retrieve medical information. Medical assistance server 135-*a* may be an example of aspects of central station 135. Based on the identity of the user transmitting the audio request and the content of the response to the audio request (e.g., if the response includes medical information), medical assistance server 135-*b* may authenticate the user to access the information requested.

Medical assistance server 135-*a* may determine if the audio request includes medical information associated with patient 105-*a*. For example, the request itself may contain medical information associated with the patient or the response my include medically relevant information for the patient 105-*a*. In some cases, a government regulation entity (e.g., a privacy policy) may protect medical information associated with patient 105-*a*. For example, Health Insurance Portability and Accountability Act (HIPPA) may require data privacy and security provisions to safeguard medical information associated with patient 105-*a*. Other governmental privacy or user-configured policies may govern what type of information is considered medically relevant or medically sensitive information, and the medical assistance system 200 may be configured to comply with the policy. Medical information associated with patient 105-*a* may require authorization of the user to access the medical information requested based on the terms of the policy.

In some examples, medical assistance server 135-*a* may determine an access class associated with the information requested by the user. Medical assistance server 135-*a* may tag the information requested by the user according to a level of security required to transmit the information to the user (e.g., patient 105-*a* or user 210). For example, a request by patient 105-*a* to schedule an appointment with clinician 205 may by tagged with a low level of security due to the lack of medically relevant information included in the response. However, if patient 105-*a* requests lab results from an appointment with clinician 205, the request may be tagged with a high level of security due to medically relevant information associated with patient 105-*a* included in the response.

In some examples, medical assistance server 135-*a* may determine a permission level of the user to access the requested information based on the access class. For example, if the information requested is tagged with a high level of security (e.g., includes medically relevant information), the permission level to access the information may also be high. Alternatively, if the information requested is tagged with a low level of security (e.g., includes non-medically relevant information), the permission level to access the information may also be low. That is, user 210 may access non-medically relevant information (e.g., low access class) associated with patient 105-*a*. On the other hand, user 210 may be unable to access medically relevant information (e.g., high access class) associated with patient 105-*a*, depending on the terms of the privacy policy in place. In order to access medically relevant information associated with patient 105-*a*, the permission level may increase and an additional layer of authorization may be implemented.

The access class and permission level may determine whether the user is authorized to access the information requested. For example, medical assistance server 135-*a* may select an authentication method based on the access class of medical information, the permission level, or both. The authentication method may include voice recognition analysis of the audio request from patient 105-*a*, user 210, or clinician 205 or include facial recognition analysis of patient 105-*a*, user 210, or clinician 205. Medical assistance server 135-*a* may recognize the voice transmitting the audio request and may authorize access based on the recognition. Similarly, medical assistance server 135-*a* may recognize facial attributes of the person requesting information and may authorize access based on the recognition.

In some hospital-based monitoring system, medical assistance server 135-*a* may perform admission and discharge functions. In some cases, medical assistance server 135-*a* may perform intake tasks associated with a new patient 105-*a*. For example, medical assistance server 135-*a* may set up the new patient 105-*a* in the system (e.g., input general medical information associated with patient 105-*a*) or assign clinician 205 to patient 105-*a*. In other examples, medical assistance server 135-*a* may determine a discharge status of patient 105-*a* from the hospital based on the medical condition of patient 105-*a*.

In some examples, the authentication method may include detecting a proximity of patient 105-*a*, user 210, or clinician 205 to a system that receives the audio request (e.g., medical audio device 115-*c*). Proximity of patient 105-*a* may be detected based on radio frequency (RF) signaling between the medical device 110-*a* associated with patient 105-*a* and medical audio device 115-*c*. The proximity may also be detected based on RF signaling between a device other than medical device 110-*a* associated with patient 105-*a* and medical audio device 115-*c*. In some case, RF signaling may be an example of Bluetooth signaling. In some hospital-based monitoring systems, medical assistance server 135-*a* may determine a location of patient 105-*a* or clinician 205 based on a previous detection of the proximity of patient 105-*a* or clinician 205 to the system that receives the audio request.

Based on the access class and the permission level, medical assistance server 135-*a* may request an additional authorization credential associated with the user accessing the information. For example, medical assistance server 135-*a* may request a fingerprint scan, a pin code input, or both. In some cases, the fingerprint scan or the pin code input may also determine the proximity of the user to the system that receives the audio request. After the user inputs the authorization credential, a timer may start to indicate an amount of time that may lapse before the user may be required to revalidate with the authorization credential.

In some cases, the authorization credential may be based on identifying a confidence level to access the information requested. That is, medical assistance server 135-*a* may identify one or more levels of confidence associated with the level of security to access the medical information. For example, to access medical information with a high level of security (e.g., a lab result), the authorization credential may include a higher confidence level as compared to accessing medical information with a low level of security (e.g., requesting a time of a scheduled appointment).

Once the user who issued the audio request has been authorized to access the relevant medical information, the medical assistance server 135-*a* may retrieve the medical information necessary to formulate a response to the request. For example, the medical assistance server 135-*a* my retrieve the medication dosage and timing schedule of the patient 105-*a* from the database 140-*a*.

Medical assistance server 135-*a* may transmit a response after determining if the user is authorized. The response may include an audio message, a visual message, or both. In some cases, the audio message may include medical information associated with patient 105-*a*, non-medical information associated with patient 105-*a* (e.g., confirmation of a scheduled appointment with clinician 205), or a voice-activated phone call. The visual message may include a video conference call. Medical assistance server 135-*a* may configure the format of the response depending on if the response is an audio message, a visual message, or both.

In some cases, the audio message may include a voice alarm. The voice alarm may indicate additional information corresponding to the alarm associated with medical device 110-*a*. For example, the voice alarm may provide additional context associated with a light, a tone, or a beep associated with the alarm. In some examples, the audio message may include a recommended action for patient 105-*a* based on the alarm. For example, if medical device 110-*a* (e.g., SpO2 sensor) associated with patient 105-*a* alarms due to low blood oxygen concentration, the audio message may include a recommendation for the patient to take deep breaths to increase the blood oxygen concentration.

In some cases, medical assistance server 135-*a* may transmit the response to clinician 205 based on a facial attribute of patient 105-*a*, a voice attribute of patient 105-*a*, or both. For example, medical assistance server 135-*a* may transmit the response to clinician 205 if medical assistance server 135-*a* detects fear, pain, or stress in the voice or facial attributes of patient 105-*a*.

Medical assistance server 135-*a* may store the audio request and the response to log the medical history of patient 105-*a*. In some cases, medical assistance server 135-*a* may retrieve the stored audio request and response based on a request to review the medical history of patient 105-*a*. For example, patient 105-*a* may receive multiple voice-initiated calls or audio messages and comment on the number of voice-initiated calls. In that case, clinician 205 or other users may retrieve the stored audio request and response to verify the reason the voice call was initiated. For example, the medical history may determine the call was initiated because medical assistance server 135-*a* detected the proximity of patient 105-*a* and a facial attribute (e.g., fear) associated with the patient condition.

Figure 3:
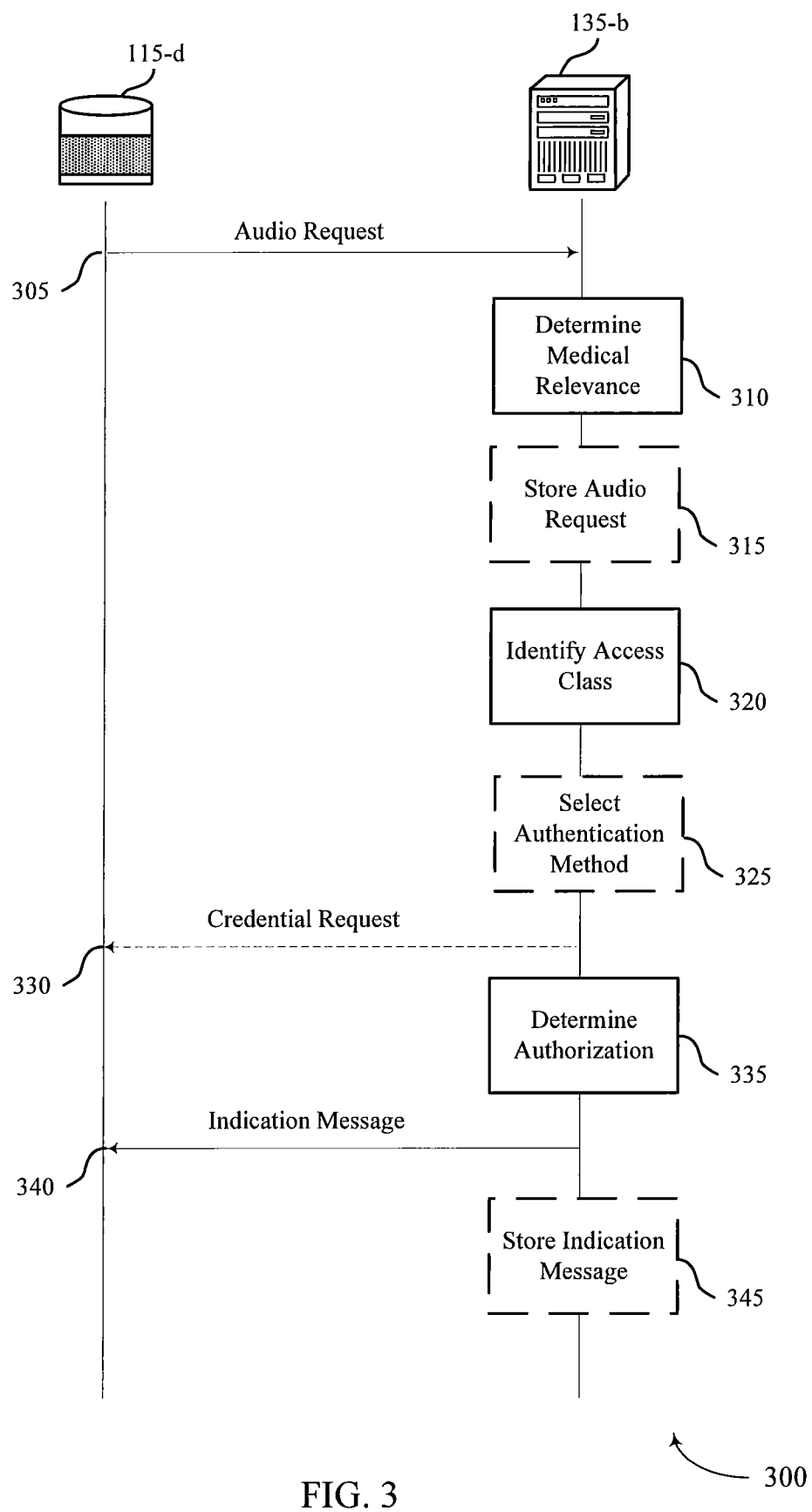
FIG. 3 illustrates an example process flow that supports automated voice-activated medical assistance in accordance with aspects of the present disclosure.

FIG. 3 illustrates an example of a process flow 300 that supports automated voice-activated medical assistance in accordance with various aspects of the present disclosure. Process flow 300 may include medical audio device 115-*d* and medical assistance server 135-*b*, which may be respective examples of a computing device 115 and central station 135 as described with reference to FIGS. 1 and 2. Alternative examples of the following may be implemented, where some steps are performed in a different order or not at all. Some steps may additionally include additional features not mentioned above.

In some examples, medical audio device 115-*d* may transmit audio request 305. In some examples, audio request 305 may be a request for medical information associated with the user, a request to schedule an appointment with a clinician, a request for medical information associated with a person other than the user, a request to initiate a call with the clinician, or a combination thereof. In some examples, an indication of the audio request 305 may be transmitted. For example, the audio request 305 may be converted into a computer-readable format using voice recognition analysis that is performed either at the medical audio device 115-*d* or at a remote server. The computer-readable format of the audio request 305 may be referred to as an indication of the audio request 305.

At block 310, medical assistance server 135-*b* may determine the medical relevance of audio request 305. For example, medical assistance server 135-*b* may determine whether a response to audio request 305 includes medical information associated with a patient. In some cases, medical assistance server 135-*b* may also determine whether audio request 305 includes a request for medical information associated with the patient (e.g., heart rate, blood glucose level, etc.). In other examples, medical assistance server 135-*b* may determine whether the medical information associated with the patient is protected by a privacy policy (e.g., HIPAA or a user-configured privacy policy).

At block 315, medical assistance server 135-*b* may store audio request 305. For example, medical assistance server 135-*b* may store audio request 305 if the response to audio request 305 includes medical information (e.g., to log a medical history). Additionally, medical assistance server 135-*b* may retrieve medical information from a database.

At block 320, medical assistance server 135-*b* may identify an access class (e.g., security level) of the medical information. Medical assistance server 135-*b* may also identify a permission level associated with accessing the access class of the medical information. In some examples, medical assistance server 135-*b* may identify a confidence level associated with the determining whether the user is authorized to access the access class.

At block 325, medical assistance server 135-*b* may select an authentication method. In some cases, the authentication method may be based on the access class of the medical information, the permission level, or both. In other examples, medical assistance server 135-*b* may determine whether the user is authorized to access the access class and authenticate the user based on the selected authentication method. An authentication method may include a voice recognition analysis of audio request 305, a facial recognition analysis of the user, determining a proximity of the user to a system that receives audio request 305, or a combination thereof.

After the authentication method is selected, medical assistance server 135-*b* may transmit credential request 330 (e.g., authorization credential). For example, credential request 330 may include a request for an authorization credential associated with the user. The authorization credential may include a finger print scan, a pin code input, or both. In some cases, the authorization credential may be based on the identified confidence level. At block 335, medical assistance server 135-*b* may determine whether the user is authorized to access the access class based on the permission level.

Medical assistance server 135-*b* may transmit indication message 340 (e.g., a response to audio request 305). In some cases, indication message 340 may be transmitted based on determining whether the user is authorized. Indication message 340 may include an indication of the response to audio request 305. For example, the response may include a medical information response associated with the user, an appointment confirmation, a medical information response associated with a person other than the user, a voice-activated phone call, a video conference call, or a combination thereof.

In some cases, indication message 340 may be transmitted to a clinician based on a facial attribute of the user, a voice attribute of the user, or both. Medical assistance server 135-*b* may configure a format of indication message 340. For example, indication message 340 may include an audio format, a visual format, or both. At block 345, medical assistance server 135-*b* may store indication message 340.

Figure 4:
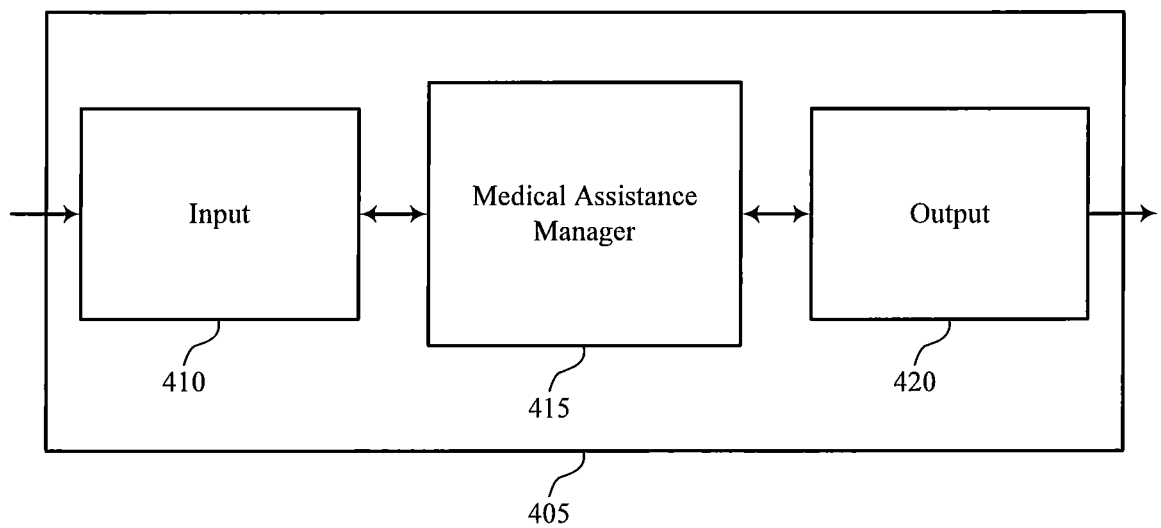
FIGS. 4 through 6 show block diagrams of a device that supports automated voice-activated medical assistance in accordance with aspects of the present disclosure.

FIG. 4 shows a block diagram 400 of a device 405 that supports automated voice-activated medical assistance in accordance with aspects of the present disclosure. Device 405 may be an example of aspects of a medical assistance server as described herein. Device 405 may include input 410, medical assistance manager 415, and output 420. Device 405 may also include a processor. Each of these components may be in communication with one another (e.g., via one or more buses).

Medical assistance manager 415 may be an example of aspects of the medical assistance manager 715 described with reference to FIG. 7.

Medical assistance manager 415 and/or at least some of its various sub-components may be implemented in hardware, software executed by a processor, firmware, or any combination thereof. If implemented in software executed by a processor, the functions of the medical assistance manager 415 and/or at least some of its various sub-components may be executed by a general-purpose processor, a digital signal processor (DSP), an application-specific integrated circuit (ASIC), an field-programmable gate array (FPGA) or other programmable logic device, discrete gate or transistor logic, discrete hardware components, or any combination thereof designed to perform the functions described in the present disclosure. The medical assistance manager 415 and/or at least some of its various sub-components may be physically located at various positions, including being distributed such that portions of functions are implemented at different physical locations by one or more physical devices. In some examples, medical assistance manager 415 and/or at least some of its various sub-components may be a separate and distinct component in accordance with various aspects of the present disclosure. In other examples, medical assistance manager 415 and/or at least some of its various sub-components may be combined with one or more other hardware components, including but not limited to an I/O component, a transceiver, a network server, another computing device, one or more other components described in the present disclosure, or a combination thereof in accordance with various aspects of the present disclosure.

Medical assistance manager 415 may receive an indication of an audio request from a user, determine whether a response to the audio request includes medical information associated with a patient, identify an access class of the medical information and a permission level associated with accessing the access class of the medical information, determine whether the user is authorized to access the access class based on the permission level, and transmit an indication of the response to the audio request based on determining whether the user is authorized.

Figure 5:
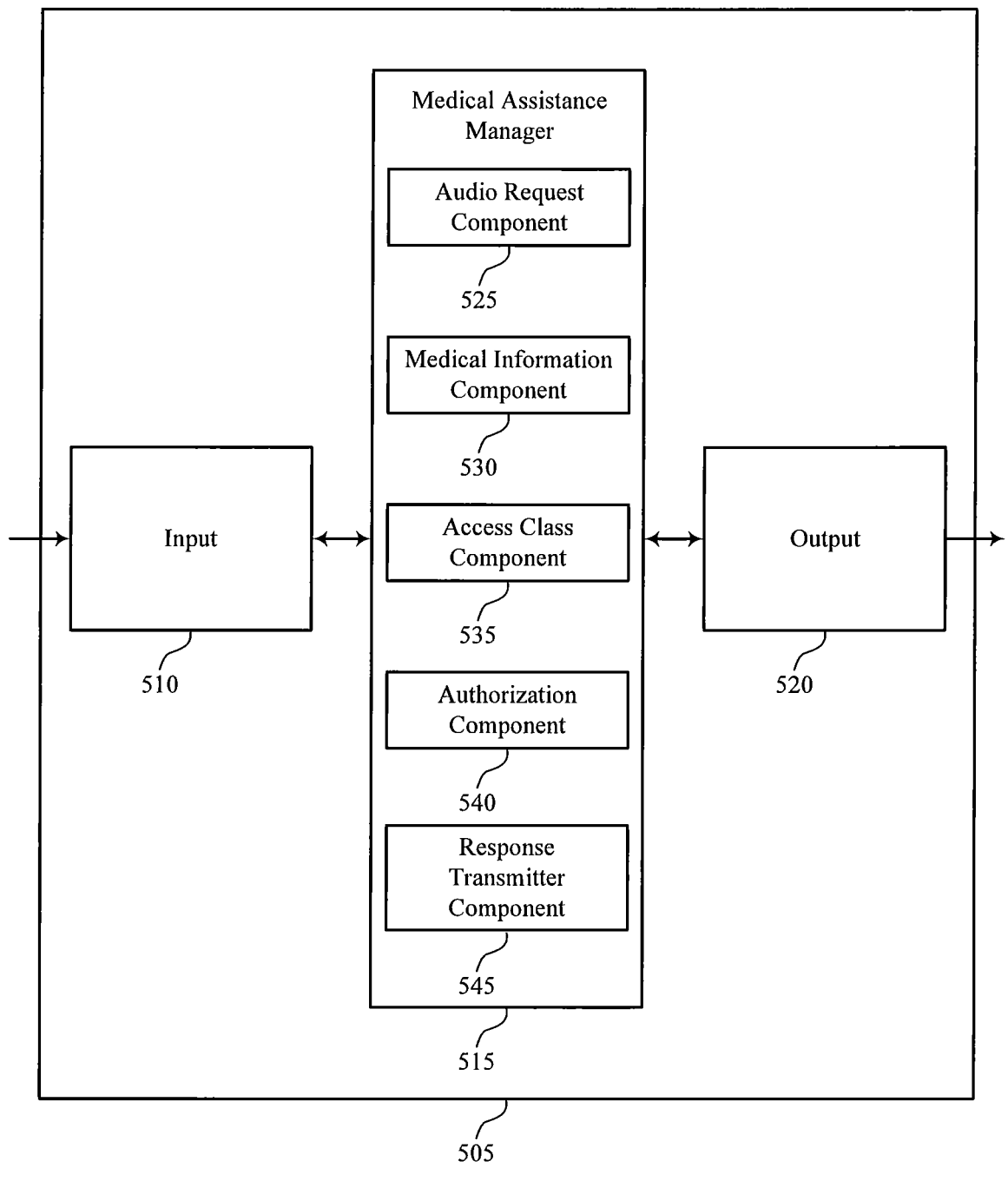

FIG. 5 shows a block diagram 500 of a device 505 that supports automated voice-activated medical assistance in accordance with aspects of the present disclosure. Device 505 may be an example of aspects of a device 405 or a medical assistance server as described with reference to FIG. 4. Device 505 may include input 510, medical assistance manager 515, and output 520. Device 505 may also include a processor. Each of these components may be in communication with one another (e.g., via one or more buses).

Medical assistance manager 515 may be an example of aspects of the medical assistance manager 715 described with reference to FIG. 7.

Medical assistance manager 515 may also include audio request component 525, medical information component 530, access class component 535, authorization component 540, and response transmitter component 545.

Audio request component 525 may receive an indication of an audio request from a user. In some cases, the audio request includes a request for medical information associated with the user, a request to schedule an appointment with a clinician, a request for medical information associated with a person other than the user, a request to initiate a call with the clinician, or a combination thereof.

Medical information component 530 may determine whether a response to the audio request includes medical information associated with a patient, determine whether the audio request includes a medical information request associated with the patient, determine whether the medical information associated with the patient is protected by a privacy policy, and retrieve the medical information from a database.

Access class component 535 may identify an access class of the medical information and a permission level associated with accessing the access class of the medical information.

Authorization component 540 may select an authentication method based on the access class of the medical information, the permission level, or both, where determining whether the user is authorized to access the access class includes authenticating the user based on the selected authentication method. Authorization component 540 may determine whether the user is authorized to access the access class based on the permission level, request an authorization credential associated with the user, where the authorization credential includes a finger print scan, a pin code input, or both. Authorization component 540 may identify a confidence level associated with the determining whether the user is authorized to access the access class, where the authorization credential is based on the identified confidence level. In some cases, the authentication method includes a voice recognition analysis of the audio request, a facial recognition analysis of the user, determining a proximity of the user to a system that receives the audio request, or a combination thereof.

Response transmitter component 545 may transmit an indication of the response to the audio request based on determining whether the user is authorized, transmit the indication of the response to a clinician based on a facial attribute of the user, a voice attribute of the user, or both, and configure a format of the indication of the response, where the format of the indication includes an audio format, a visual format, or both. In some cases, the response includes a medical information response associated with the user, an appointment confirmation, a medical information response associated with a person other than the user, a voice-activated phone call, a video conference call, or a combination thereof.

Figure 6:
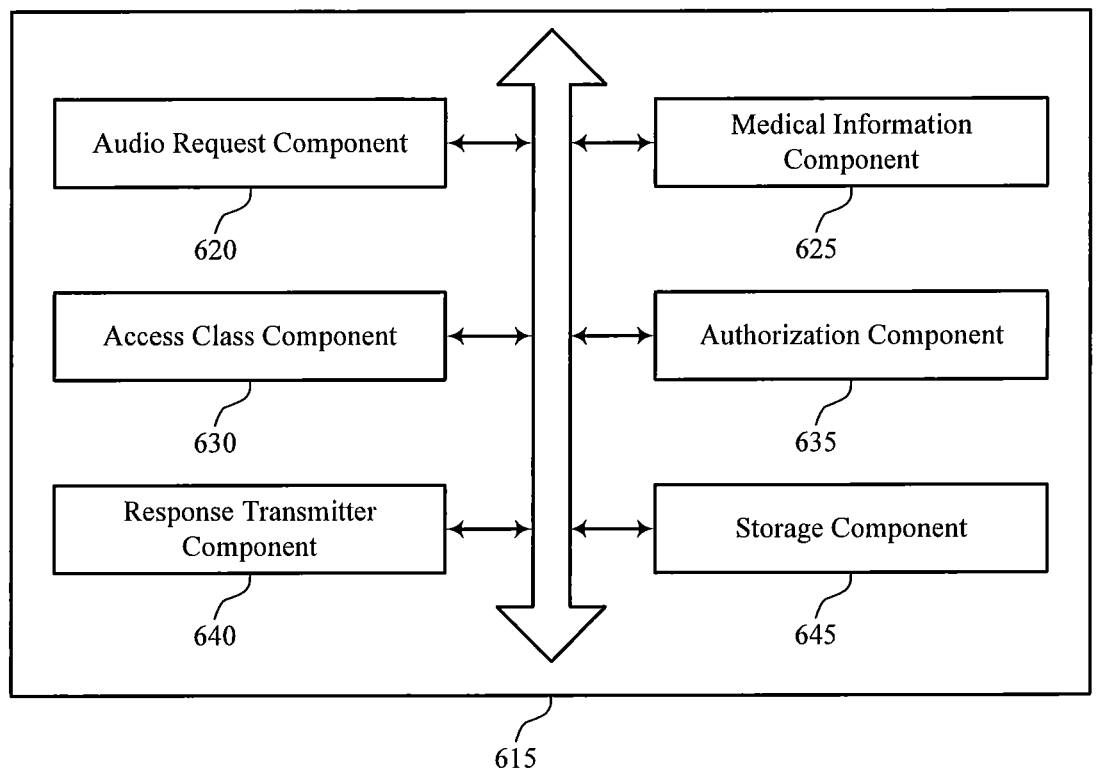

FIG. 6 shows a block diagram 600 of a medical assistance manager 615 that supports automated voice-activated medical assistance in accordance with aspects of the present disclosure. The medical assistance manager 615 may be an example of aspects of a medical assistance manager 415, a medical assistance manager 515, or a medical assistance manager 715 described with reference to FIGS. 4, 5, and 7. The medical assistance manager 615 may include audio request component 620, medical information component 625, access class component 630, authorization component 635, response transmitter component 640, and storage component 645. Each of these modules may communicate, directly or indirectly, with one another (e.g., via one or more buses).

Audio request component 620 may receive an indication of an audio request from a user. In some cases, the audio request includes a request for medical information associated with the user, a request to schedule an appointment with a clinician, a request for medical information associated with a person other than the user, a request to initiate a call with the clinician, or a combination thereof.

Medical information component 625 may determine whether a response to the audio request includes medical information associated with a patient, determine whether the audio request includes a medical information request associated with the patient, determine whether the medical information associated with the patient is protected by a privacy policy, and retrieve the medical information from a database.

Access class component 630 may identify an access class of the medical information and a permission level associated with accessing the access class of the medical information.

Authorization component 635 may select an authentication method based on the access class of the medical information, the permission level, or both, where determining whether the user is authorized to access the access class includes authenticating the user based on the selected authentication method. Authorization component 635 may determine whether the user is authorized to access the access class based on the permission level, request an authorization credential associated with the user, where the authorization credential includes a finger print scan, a pin code input, or both. Authorization component 635 may identify a confidence level associated with the determining whether the user is authorized to access the access class, where the authorization credential is based on the identified confidence level. In some cases, the authentication method includes a voice recognition analysis of the audio request, a facial recognition analysis of the user, determining a proximity of the user to a system that receives the audio request, or a combination thereof.

Response transmitter component 640 may transmit an indication of the response to the audio request based on determining whether the user is authorized, transmit the indication of the response to a clinician based on a facial attribute of the user, a voice attribute of the user, or both, and configure a format of the indication of the response, where the format of the indication includes an audio format, a visual format, or both. In some cases, the response includes a medical information response associated with the user, an appointment confirmation, a medical information response associated with a person other than the user, a voice-activated phone call, a video conference call, or a combination thereof.

Storage component 645 may store the indication of the audio request if the response to the audio request includes medical information associated with the patient and store the indication of the response to the audio request.

Figure 7:
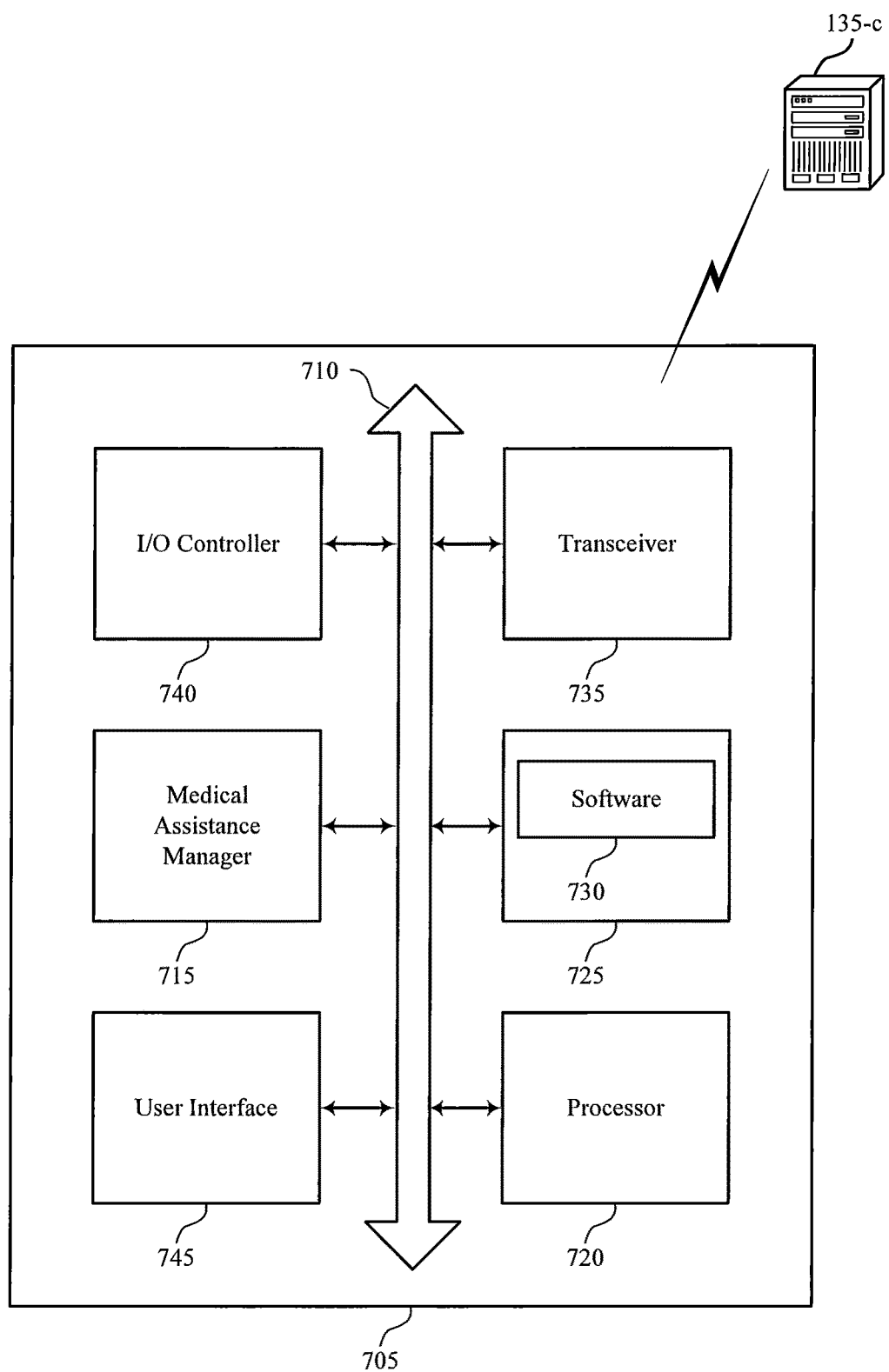
FIG. 7 illustrates a block diagram of a system including a medical assistance server that supports automated voice-activated medical assistance in accordance with aspects of the present disclosure.

FIG. 7 shows a diagram of a system 700 including a device 705 that supports automated voice-activated medical assistance in accordance with aspects of the present disclosure. Device 705 may be an example of or include the components of device 405, device 505, or a medical assistance server as described above, e.g., with reference to FIGS. 4 and 5. Device 705 may include components for bi-directional voice and data communications including components for transmitting and receiving communications, including medical assistance manager 715, processor 720, memory 725, software 730, transceiver 735, I/O controller 740, and user interface 745. These components may be in electronic communication via one or more buses (e.g., bus 710).

Processor 720 may include an intelligent hardware device, (e.g., a general-purpose processor, a DSP, a central processing unit (CPU), a microcontroller, an ASIC, an FPGA, a programmable logic device, a discrete gate or transistor logic component, a discrete hardware component, or any combination thereof). The processor 720 may process information received from medical assistance server 135-c. In some cases, processor 720 may be configured to operate a memory array using a memory controller. In other cases, a memory controller may be integrated into processor 720. Processor 720 may be configured to execute computer-readable instructions stored in a memory to perform various functions (e.g., functions or tasks supporting automated voice-activated medical assistance).

Memory 725 may include random access memory (RAM) and read only memory (ROM). The memory 725 may store computer-readable, computer-executable software 730 including instructions that, when executed, cause the processor to perform various functions described herein. In some cases, the memory 725 may contain, among other things, a basic input/output system (BIOS) which may control basic hardware or software operation such as the interaction with peripheral components or devices.

Software 730 may include code to implement aspects of the present disclosure, including code to support automated voice-activated medical assistance. Software 730 may be stored in a non-transitory computer-readable medium such as system memory or other memory. In some cases, the software 730 may not be directly executable by the processor but may cause a computer (e.g., when compiled and executed) to perform functions described herein.

Transceiver 735 may communicate bi-directionally, via one or more antennas, wired, or wireless links as described above. For example, the transceiver 735 may represent a wireless transceiver and may communicate bi-directionally with another wireless transceiver. The transceiver 735 may also include a modem to modulate the packets and provide the modulated packets to the antennas for transmission, and to demodulate packets received from the antennas.

I/O controller 740 may manage input and output signals for device 705. I/O controller 740 may also manage peripherals not integrated into device 705. In some cases, I/O controller 740 may represent a physical connection or port to an external peripheral. In some cases, I/O controller 740 may utilize an operating system such as iOS®, ANDROID®, MS-DOS®, MS-WINDOWS®, OS/2®, UNIX®, LINUX®, or another known operating system. In other cases, I/O controller 740 may represent or interact with a modem, a keyboard, a mouse, a touchscreen, or a similar device. In some cases, I/O controller 740 may be implemented as part of a processor. In some cases, a user may interact with device 705 via I/O controller 740 or via hardware components controlled by I/O controller 740.

User interface 745 may enable a user to interact with device 705. In some embodiments, the user interface module 745 may include an audio device, such as an external speaker system, an external display device such as a display screen, or an input device (e.g., remote control device interfaced with the user interface module 745 directly or through the I/O controller module).

Figure 8:
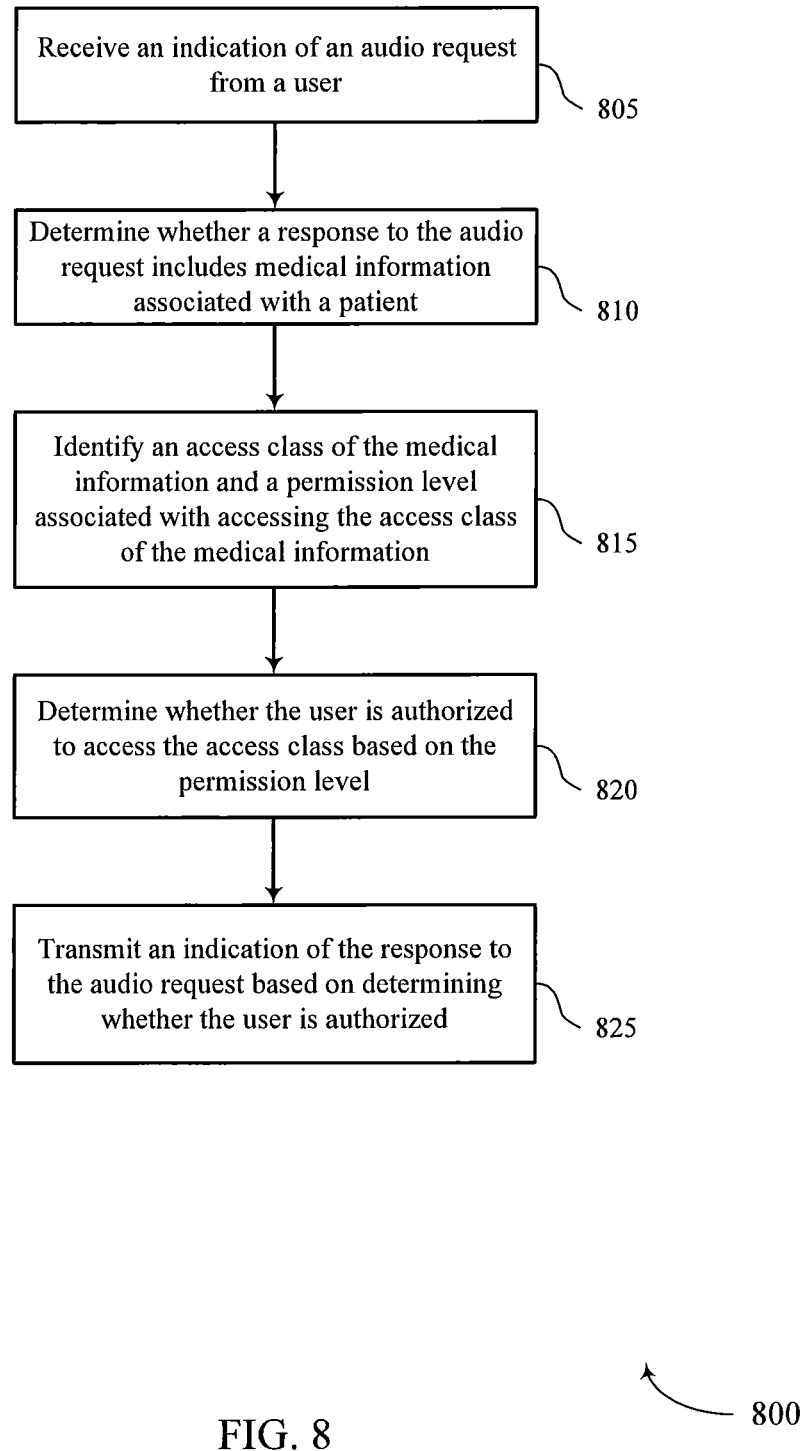
FIGS. 8 through 12 illustrate methods for automated voice-activated medical assistance in accordance with aspects of the present disclosure.

FIG. 8 shows a flowchart illustrating a method 800 for automated voice-activated medical assistance in accordance with aspects of the present disclosure. The operations of method 800 may be implemented by a medical assistance server or its components as described herein. For example, the operations of method 800 may be performed by a medical assistance manager as described with reference to FIGS. 4 through 7. In some examples, a medical assistance server may execute a set of codes to control the functional elements of the device to perform the functions described below. Additionally or alternatively, the medical assistance server may perform aspects of the functions described below using special-purpose hardware.

At 805 the medical assistance server may receive an indication of an audio request from a user. The operations of 805 may be performed according to the methods described herein. In certain examples, aspects of the operations of 805 may be performed by an audio request component as described with reference to FIGS. 4 through 7.

At 810 the medical assistance server may determine whether a response to the audio request includes medical information associated with a patient. The operations of 810 may be performed according to the methods described herein. In certain examples, aspects of the operations of 810 may be performed by a medical information component as described with reference to FIGS. 4 through 7.

At 815 the medical assistance server may identify an access class of the medical information and a permission level associated with accessing the access class of the medical information. The operations of 815 may be performed according to the methods described herein. In certain examples, aspects of the operations of 815 may be performed by an access class component as described with reference to FIGS. 4 through 7.

At 820 the medical assistance server may determine whether the user is authorized to access the access class based at least in part on the permission level. The operations of 820 may be performed according to the methods described herein. In certain examples, aspects of the operations of 820 may be performed by an authorization component as described with reference to FIGS. 4 through 7.

At 825 the medical assistance server may transmit an indication of the response to the audio request based at least in part on determining whether the user is authorized. The operations of 825 may be performed according to the methods described herein. In certain examples, aspects of the operations of 825 may be performed by a response transmitter component as described with reference to FIGS. 4 through 7.

Figure 9:
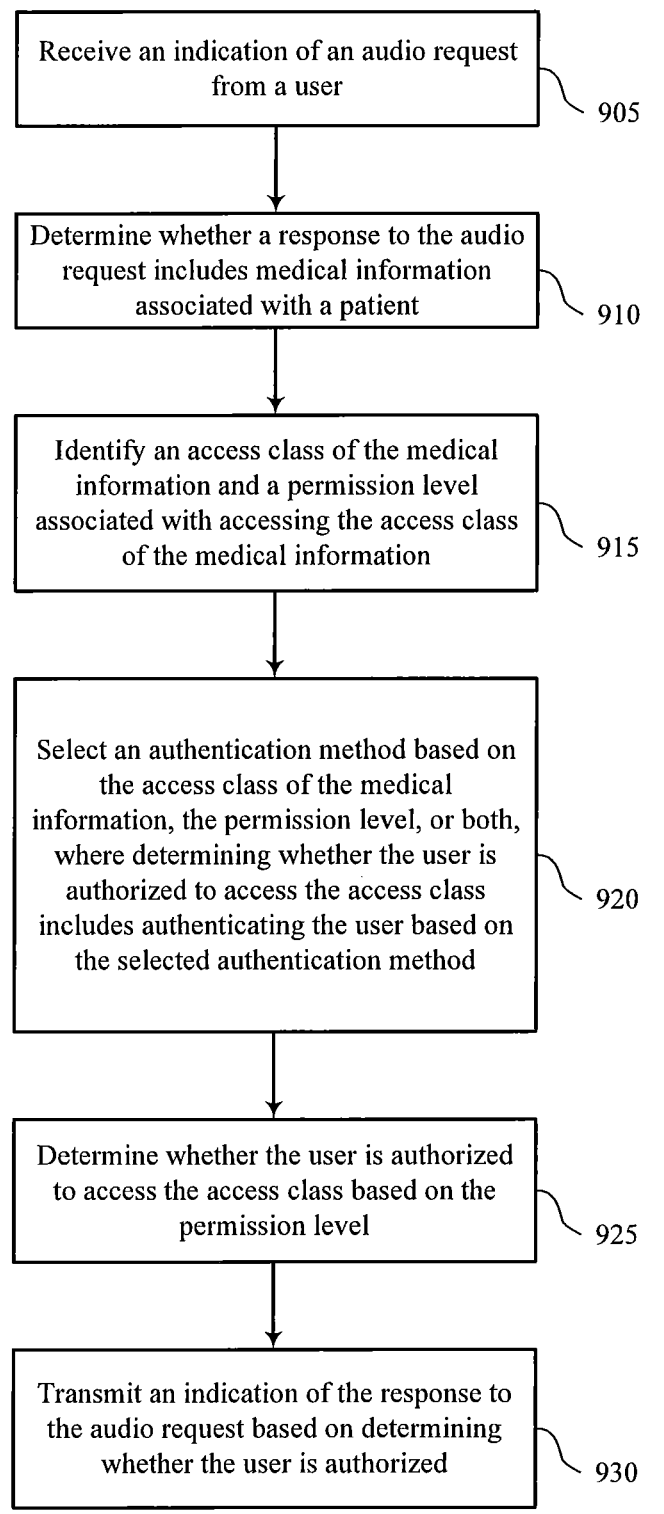

FIG. 9 shows a flowchart illustrating a method 900 for automated voice-activated medical assistance in accordance with aspects of the present disclosure. The operations of method 900 may be implemented by a medical assistance server or its components as described herein. For example, the operations of method 900 may be performed by a medical assistance manager as described with reference to FIGS. 4 through 7. In some examples, a medical assistance server may execute a set of codes to control the functional elements of the device to perform the functions described below. Additionally or alternatively, the medical assistance server may perform aspects of the functions described below using special-purpose hardware.

At 905 the medical assistance server may receive an indication of an audio request from a user. The operations of 905 may be performed according to the methods described herein. In certain examples, aspects of the operations of 905 may be performed by an audio request component as described with reference to FIGS. 4 through 7.

At 910 the medical assistance server may determine whether a response to the audio request includes medical information associated with a patient. The operations of 910 may be performed according to the methods described herein. In certain examples, aspects of the operations of 910 may be performed by a medical information component as described with reference to FIGS. 4 through 7.

At 915 the medical assistance server may identify an access class of the medical information and a permission level associated with accessing the access class of the medical information. The operations of 915 may be performed according to the methods described herein. In certain examples, aspects of the operations of 915 may be performed by an access class component as described with reference to FIGS. 4 through 7.

At 920 the medical assistance server may select an authentication method based at least in part on the access class of the medical information, the permission level, or both, wherein determining whether the user is authorized to access the access class comprises authenticating the user based at least in part on the selected authentication method. The operations of 920 may be performed according to the methods described herein. In certain examples, aspects of the operations of 920 may be performed by an authorization component as described with reference to FIGS. 4 through 7.

At 925 the medical assistance server may determine whether the user is authorized to access the access class based at least in part on the permission level. The operations of 925 may be performed according to the methods described herein. In certain examples, aspects of the operations of 925 may be performed by an authorization component as described with reference to FIGS. 4 through 7.

At 930 the medical assistance server may transmit an indication of the response to the audio request based at least in part on determining whether the user is authorized. The operations of 930 may be performed according to the methods described herein. In certain examples, aspects of the operations of 930 may be performed by a response transmitter component as described with reference to FIGS. 4 through 7.

Figure 10:
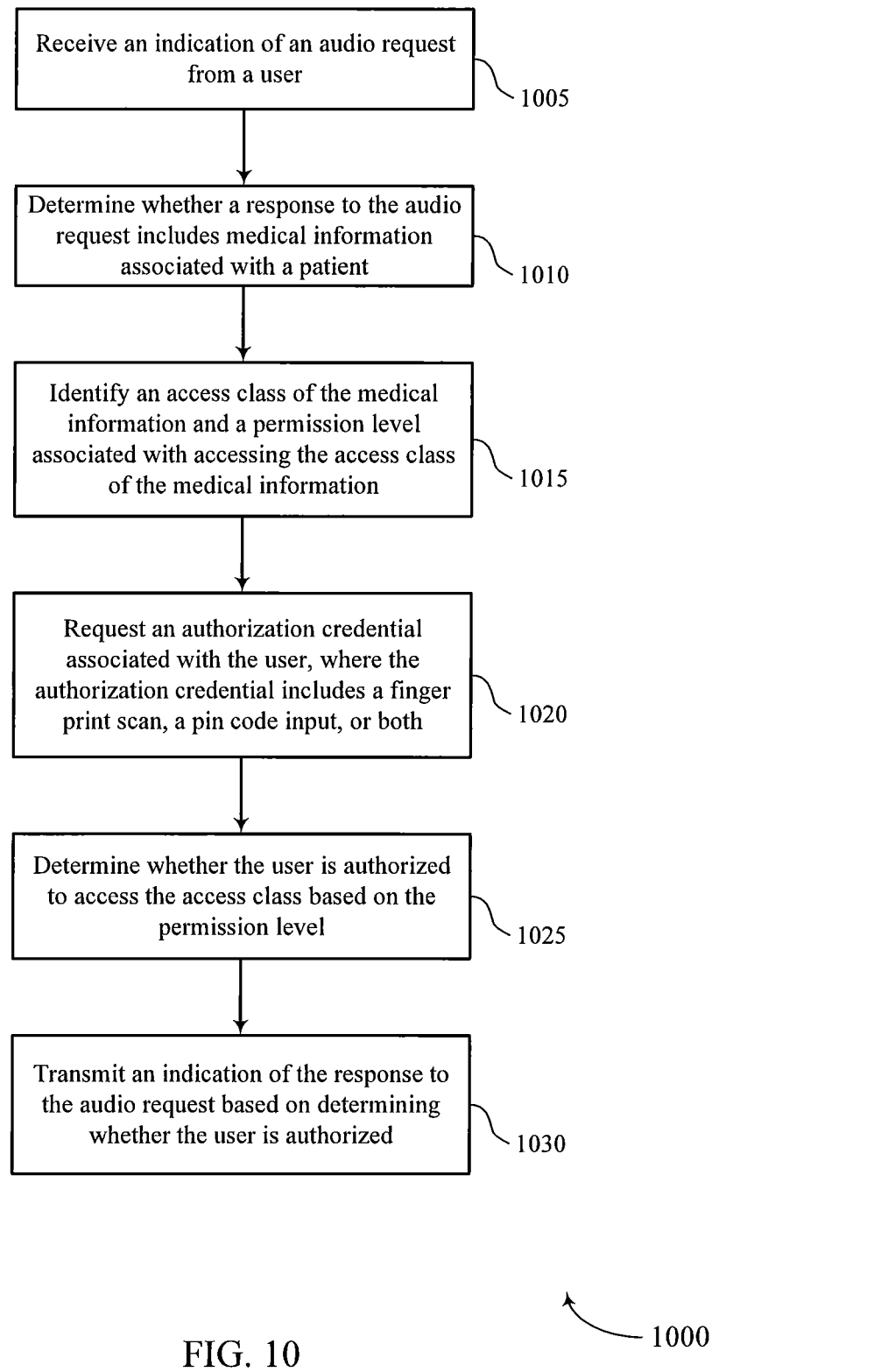

FIG. 10 shows a flowchart illustrating a method 1000 for automated voice-activated medical assistance in accordance with aspects of the present disclosure. The operations of method 1000 may be implemented by a medical assistance server or its components as described herein. For example, the operations of method 1000 may be performed by a medical assistance manager as described with reference to FIGS. 4 through 7. In some examples, a medical assistance server may execute a set of codes to control the functional elements of the device to perform the functions described below. Additionally or alternatively, the medical assistance server may perform aspects of the functions described below using special-purpose hardware.

At 1005 the medical assistance server may receive an indication of an audio request from a user. The operations of 1005 may be performed according to the methods described herein. In certain examples, aspects of the operations of 1005 may be performed by an audio request component as described with reference to FIGS. 4 through 7.

At 1010 the medical assistance server may determine whether a response to the audio request includes medical information associated with a patient. The operations of 1010 may be performed according to the methods described herein. In certain examples, aspects of the operations of 1010 may be performed by a medical information component as described with reference to FIGS. 4 through 7.

At 1015 the medical assistance server may identify an access class of the medical information and a permission level associated with accessing the access class of the medical information. The operations of 1015 may be performed according to the methods described herein. In certain examples, aspects of the operations of 1015 may be performed by an access class component as described with reference to FIGS. 4 through 7.

At 1020 the medical assistance server may request an authorization credential associated with the user, wherein the authorization credential comprises a finger print scan, a pin code input, or both. The operations of 1020 may be performed according to the methods described herein. In certain examples, aspects of the operations of 1020 may be performed by an authorization component as described with reference to FIGS. 4 through 7.

At 1025 the medical assistance server may determine whether the user is authorized to access the access class based at least in part on the permission level. The operations of 1025 may be performed according to the methods described herein. In certain examples, aspects of the operations of 1025 may be performed by an authorization component as described with reference to FIGS. 4 through 7.

At 1030 the medical assistance server may transmit an indication of the response to the audio request based at least in part on determining whether the user is authorized. The operations of 1030 may be performed according to the methods described herein. In certain examples, aspects of the operations of 1030 may be performed by a response transmitter component as described with reference to FIGS. 4 through 7.

Figure 11:
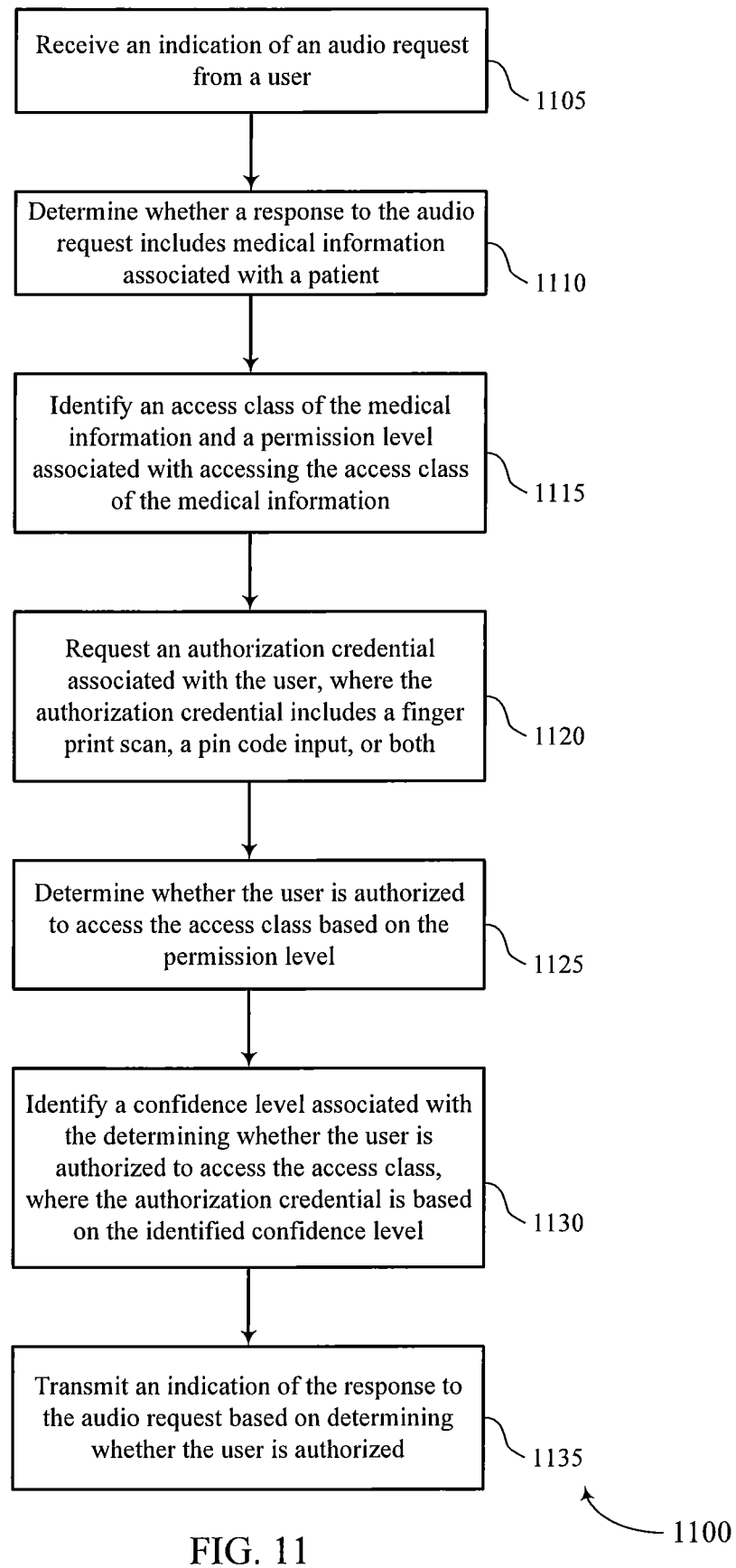

FIG. 11 shows a flowchart illustrating a method 1100 for automated voice-activated medical assistance in accordance with aspects of the present disclosure. The operations of method 1100 may be implemented by a medical assistance server or its components as described herein. For example, the operations of method 1100 may be performed by a medical assistance manager as described with reference to FIGS. 4 through 7. In some examples, a medical assistance server may execute a set of codes to control the functional elements of the device to perform the functions described below. Additionally or alternatively, the medical assistance server may perform aspects of the functions described below using special-purpose hardware.

At 1105 the medical assistance server may receive an indication of an audio request from a user. The operations of 1105 may be performed according to the methods described herein. In certain examples, aspects of the operations of 1105 may be performed by an audio request component as described with reference to FIGS. 4 through 7.

At 1110 the medical assistance server may determine whether a response to the audio request includes medical information associated with a patient. The operations of 1110 may be performed according to the methods described herein. In certain examples, aspects of the operations of 1110 may be performed by a medical information component as described with reference to FIGS. 4 through 7.

At 1115 the medical assistance server may identify an access class of the medical information and a permission level associated with accessing the access class of the medical information. The operations of 1115 may be performed according to the methods described herein. In certain examples, aspects of the operations of 1115 may be performed by an access class component as described with reference to FIGS. 4 through 7.

At 1120 the medical assistance server may request an authorization credential associated with the user, wherein the authorization credential comprises a finger print scan, a pin code input, or both. The operations of 1120 may be performed according to the methods described herein. In certain examples, aspects of the operations of 1120 may be performed by an authorization component as described with reference to FIGS. 4 through 7.

At 1125 the medical assistance server may determine whether the user is authorized to access the access class based at least in part on the permission level. The operations of 1125 may be performed according to the methods described herein. In certain examples, aspects of the operations of 1125 may be performed by an authorization component as described with reference to FIGS. 4 through 7.

At 1130 the medical assistance server may identify a confidence level associated with the determining whether the user is authorized to access the access class, wherein the authorization credential is based at least in part on the identified confidence level. The operations of 1130 may be performed according to the methods described herein. In certain examples, aspects of the operations of 1130 may be performed by an authorization component as described with reference to FIGS. 4 through 7.

At 1135 the medical assistance server may transmit an indication of the response to the audio request based at least in part on determining whether the user is authorized. The operations of 1135 may be performed according to the methods described herein. In certain examples, aspects of the operations of 1135 may be performed by a response transmitter component as described with reference to FIGS. 4 through 7.

Figure 12:
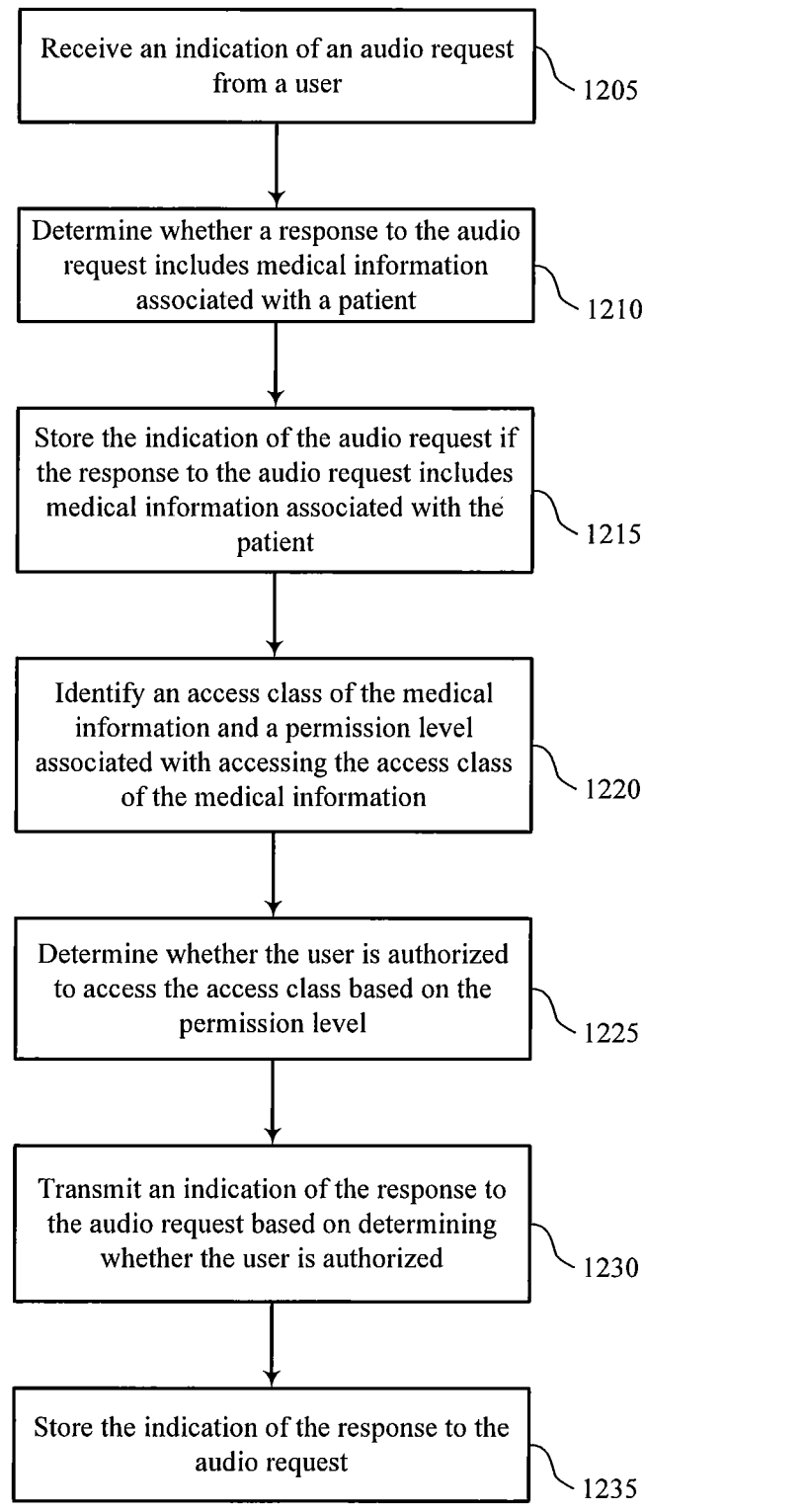

FIG. 12 shows a flowchart illustrating a method 1200 for automated voice-activated medical assistance in accordance with aspects of the present disclosure. The operations of method 1200 may be implemented by a medical assistance server or its components as described herein. For example, the operations of method 1200 may be performed by a medical assistance manager as described with reference to FIGS. 4 through 7. In some examples, a medical assistance server may execute a set of codes to control the functional elements of the device to perform the functions described below. Additionally or alternatively, the medical assistance server may perform aspects of the functions described below using special-purpose hardware.

At 1205 the medical assistance server may receive an indication of an audio request from a user. The operations of 1205 may be performed according to the methods described herein. In certain examples, aspects of the operations of 1205 may be performed by an audio request component as described with reference to FIGS. 4 through 7.

At 1210 the medical assistance server may determine whether a response to the audio request includes medical information associated with a patient. The operations of 1210 may be performed according to the methods described herein. In certain examples, aspects of the operations of 1210 may be performed by a medical information component as described with reference to FIGS. 4 through 7.

At 1215 the medical assistance server may store the indication of the audio request if the response to the audio request includes medical information associated with the patient. The operations of 1215 may be performed according to the methods described herein. In certain examples, aspects of the operations of 1215 may be performed by a storage component as described with reference to FIGS. 4 through 7.

At 1220 the medical assistance server may identify an access class of the medical information and a permission level associated with accessing the access class of the medical information. The operations of 1220 may be performed according to the methods described herein. In certain examples, aspects of the operations of 1220 may be performed by an access class component as described with reference to FIGS. 4 through 7.

At 1225 the medical assistance server may determine whether the user is authorized to access the access class based at least in part on the permission level. The operations of 1225 may be performed according to the methods described herein. In certain examples, aspects of the operations of 1225 may be performed by an authorization component as described with reference to FIGS. 4 through 7.

At 1230 the medical assistance server may transmit an indication of the response to the audio request based at least in part on determining whether the user is authorized. The operations of 1230 may be performed according to the methods described herein. In certain examples, aspects of the operations of 1230 may be performed by a response transmitter component as described with reference to FIGS. 4 through 7.

At 1235 the medical assistance server may store the indication of the response to the audio request. The operations of 1235 may be performed according to the methods described herein. In certain examples, aspects of the operations of 1235 may be performed by a storage component as described with reference to FIGS. 4 through 7.

It should be noted that the methods described above describe possible implementations, and that the operations and the steps may be rearranged or otherwise modified and that other implementations are possible. Furthermore, aspects from two or more of the methods may be combined.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a digital signal processor (DSP), an ASIC, an field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration). A processor may in some cases be in electronic communication with a memory, where the memory stores instructions that are executable by the processor. Thus, the functions described herein may be performed by one or more other processing units (or cores), on at least one integrated circuit (IC). In various examples, different types of ICs may be used (e.g., Structured/Platform ASICs, an FPGA, or another semi-custom IC), which may be programmed in any manner known in the art. The functions of each unit may also be implemented, in whole or in part, with instructions embodied in a memory, formatted to be executed by one or more general or application-specific processors.

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above may be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media may comprise RAM, ROM, electrically erasable programmable read only memory (EEPROM), compact disk (CD) ROM or other optical disk storage, magnetic disk storage or other magnetic storage devices, or any other non-transitory medium that may be used to carry or store desired program code means in the form of instructions or data structures and that may be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, digital subscriber line (DSL), or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A method for voice-activated medical assistance, comprising:
    receiving an indication of an audio request from a user;
    determining whether a response to the audio request includes medical information associated with a patient;
    identifying an access class of the medical information included in the response to the audio request after determining whether the response to the audio request includes the medical information;
    identifying a permission level associated with accessing the access class of the medical information included in the response to the audio request after determining whether the response to the audio request includes the medical information;
    determining whether the user is authorized to access the access class based at least in part on the permission level, wherein determining whether the user is authorized further comprises identifying a confidence level associated with determining whether the user is authorized to access the access class of the medical information included in the response to the audio request; and
    transmitting an indication of the response to the audio request based at least in part on determining whether the user is authorized.

2. The method of claim 1, further comprising:
    selecting an authentication method based at least in part on the access class of the medical information, the permission level, or both, wherein determining whether the user is authorized to access the access class comprises authenticating the user based at least in part on the selected authentication method.

3. The method of claim 2, wherein the authentication method comprises a voice recognition analysis of the audio request, a facial recognition analysis of the user, determining a proximity of the user to a system that receives the audio request, or a combination thereof.

4. The method of claim 1, further comprising:
    requesting an authorization credential associated with the user based at least in part on the identified confidence level, wherein the authorization credential comprises a finger print scan, a pin code input, or both.

5. The method of claim 1, further comprising:
    determining whether the audio request includes a medical information request associated with the patient.

6. The method of claim 1, further comprising:
    determining whether the medical information associated with the patient is protected by a privacy policy.

7. The method of claim 1, further comprising:
    storing the indication of the audio request if the response to the audio request includes the medical information associated with the patient; and
    storing the indication of the response to the audio request.

8. The method of claim 1, further comprising:
    retrieving the medical information from a database.

9. The method of claim 1, further comprising:
    transmitting the indication of the response to a clinician based at least in part on a facial attribute of the user, a voice attribute of the user, or both.

10. The method of claim 1, further comprising:
    configuring a format of the indication of the response, wherein the format of the indication comprises an audio format, a visual format, or both.

11. The method of claim 1, wherein the audio request comprises a request for medical information associated with the user, a request to schedule an appointment with a clinician, a request for medical information associated with a person other than the user, a request to initiate a call with the clinician, or a combination thereof.

12. The method of claim 1, wherein the response comprises a medical information response associated with the user, an appointment confirmation, a medical information response associated with a person other than the user, a voice-activated phone call, a video conference call, or a combination thereof.

13. An apparatus for voice-activated medical assistance, comprising:
    a processor;
    memory in electronic communication with the processor; and
    instructions stored in the memory and executable by the processor to cause the apparatus to:
    receive an indication of an audio request from a user;
    determine whether a response to the audio request includes medical information associated with a patient;
    identify an access class of the medical information included in the response to the audio request after determining whether the response to the audio request includes the medical information;
    identify a permission level associated with accessing the access class of the medical information included in the response to the audio request after determining whether the response to the audio request includes the medical information;
    determine whether the user is authorized to access the access class based at least in part on the permission level, wherein determining whether the user is authorized further comprises identifying a confidence level associated with determining whether the user is authorized to access the access class of the medical information included in the response to the audio request; and
    transmit an indication of the response to the audio request based at least in part on determining whether the user is authorized.

14. The apparatus of claim 13, wherein the instructions are further executable by the processor to cause the apparatus to:
    select an authentication method based at least in part on the access class of the medical information, the permission level, or both, wherein determining whether the user is authorized to access the access class comprises authenticating the user based at least in part on the selected authentication method.

15. The apparatus of claim 14, wherein the authentication method comprises a voice recognition analysis of the audio request, a facial recognition analysis of the user, determining a proximity of the user to a system that receives the audio request, or a combination thereof.

16. The apparatus of claim 13, wherein the instructions are further executable by the processor to cause the apparatus to:
request an authorization credential associated with the user based at least in part on the identified confidence level, wherein the authorization credential comprises a finger print scan, a pin code input, or both.

17. The apparatus of claim 13, wherein the instructions are further executable by the processor to cause the apparatus to:
store the indication of the audio request if the response to the audio request includes medical information associated with the patient; and
store the indication of the response to the audio request.

18. A non-transitory computer readable medium storing code for voice-activated medical assistance, the code comprising instructions executable by a processor to:
receive an indication of an audio request from a user;
determine whether a response to the audio request includes medical information associated with a patient;
identify an access class of the medical information included in the response to the audio request after determining whether the response to the audio request includes the medical information;
identify a permission level associated with accessing the access class of the medical information included in the response to the audio request after determining whether the response to the audio request includes the medical information;
determine whether the user is authorized to access the access class based at least in part on the permission level, wherein determining whether the user is authorized further comprises identifying a confidence level associated with determining whether the user is authorized to access the access class of the medical information included in the response to the audio request; and
transmit an indication of the response to the audio request based at least in part on determining whether the user is authorized.

* * * * *